United States Patent [19]

Peterson et al.

[11] 4,143,540

[45] Mar. 13, 1979

[54] METHOD OF PREVENTING CORROSION OF JOINTS OF STEEL STRUCTURES SUBMERGED IN CORROSIVE MEDIA

[75] Inventors: Marvin L. Peterson; Donald H. Oertle, both of Ponca City, Okla.

[73] Assignee: Continental Oil Company, Ponca City, Okla.

[21] Appl. No.: 864,574

[22] Filed: Dec. 27, 1977

[51] Int. Cl.² .................... G01M 3/14; G01N 33/20
[52] U.S. Cl. .................................. 73/40; 73/46; 405/195
[58] Field of Search .................. 73/40, 46; 61/54; 116/114 P

[56] References Cited

U.S. PATENT DOCUMENTS

| | | | |
|---|---|---|---|
| 2,660,053 | 11/1953 | Buehner | 73/40 |
| 2,762,736 | 9/1956 | Bueglet | 73/40 X |
| 2,817,230 | 12/1957 | McCully | 73/46 |
| 3,601,999 | 8/1971 | Olsen et al. | 61/54 X |
| 3,667,862 | 6/1972 | Parr | 73/40 X |
| 3,719,049 | 3/1973 | Shaw et al. | 61/54 |
| 4,058,985 | 11/1977 | Liddell | 61/54 |
| 4,084,430 | 4/1978 | Boyle et al. | 73/141 R |

Primary Examiner—Charles Gorenstein
Attorney, Agent, or Firm—Cortlan R. Schupbach, Jr.

[57] ABSTRACT

The integrity of corrosion prevention sheaths of corrosive-resistant metal employed to prevent member corrosion on off-shore platforms is monitored by incorporation of a pressure sensing line sealed into the zone between the sheath and the member. This apparatus allows monitoring members in the splash zone as well as stressed areas such as weld joints which are subject to corrosive environments.

9 Claims, 3 Drawing Figures

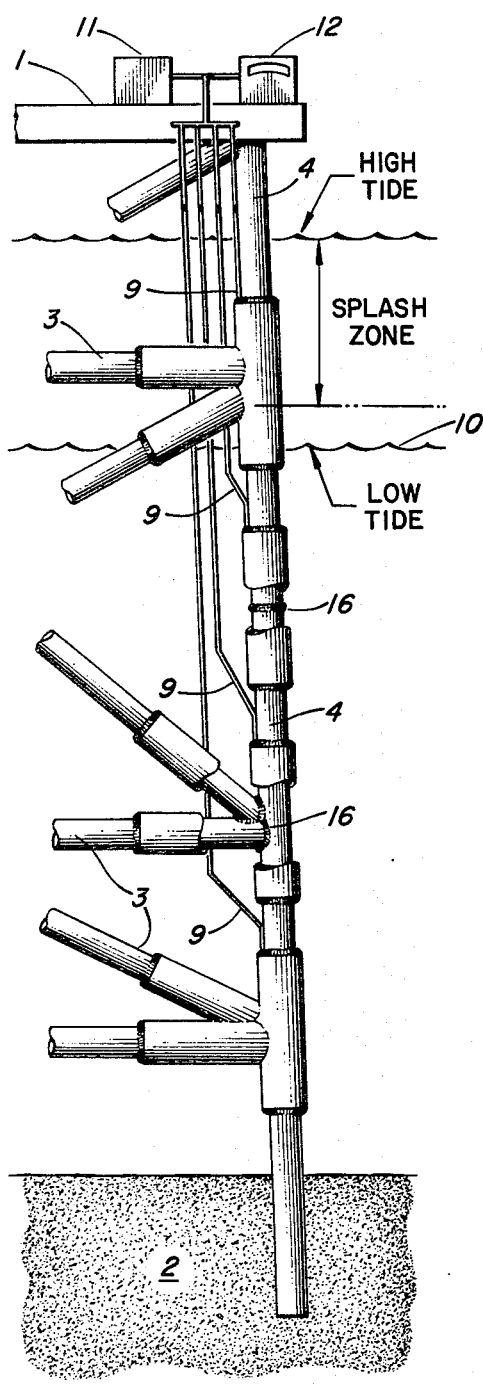
FIGURE I
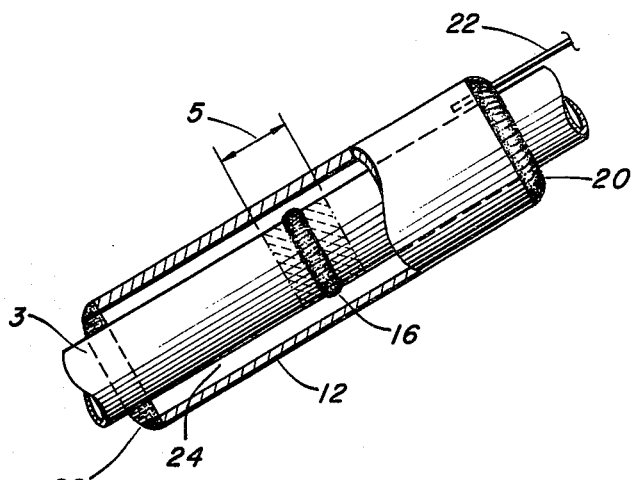
FIGURE II
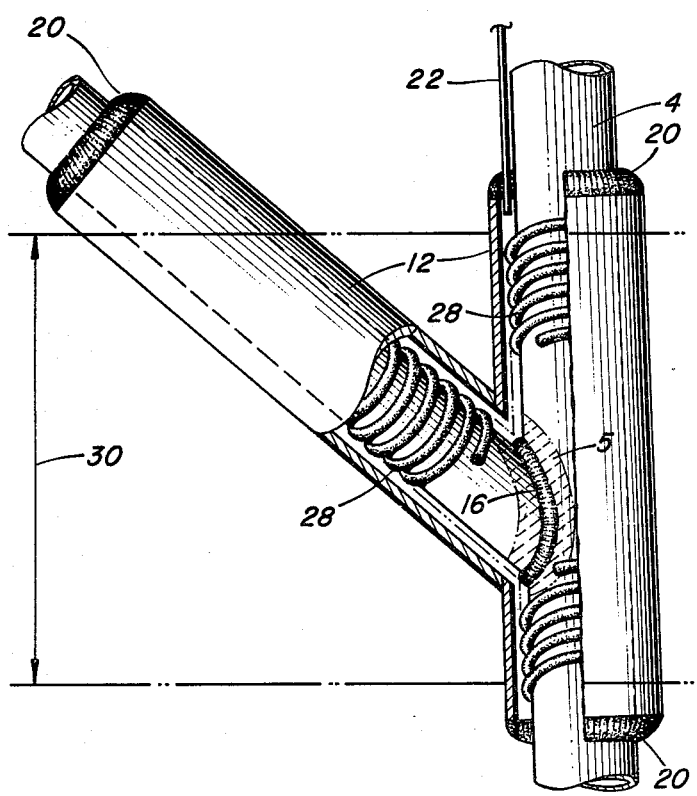
FIGURE III

METHOD OF PREVENTING CORROSION OF JOINTS OF STEEL STRUCTURES SUBMERGED IN CORROSIVE MEDIA

MONITORED CORROSION PREVENTION SHEATHS

This invention relates to a method for protecting structural members or portions of structural members of offshore steel platforms from corrosion and corrosion fatigue. More particularly, this invention relates to an improved method for monitoring corrosion protection sheaths attached to support members of offshore steel platforms subject to corrosion.

Exploration for minerals beneath bodies of water requires the use of offshore platforms. These platforms must be firmly supported to withstand the often violent weather conditions which prevail. These supports normally take a form of large steel pipes which extend from the platform to a point on the bottom of the lake or ocean floor. These members are normally of steel, and steel will corrode more severely in areas of structural welds or high stress. Other areas of high corrosion are splash zone areas which are intermittantly wet and dry and which are not entirely protected by cathodic protection. Other pipes, risers, flowlines, and the like extend from beneath the surface of the water from these offshore platforms to the deck area above the water surface.

Severe corrosion problems are often encountered with submerged offshore steel supports and flowlines. Such corrosion problems and corrosion fatigue are especially severe in the joint or weld areas of the submerged steel supports as well as splash zone areas. Failure in such localized areas is extremely rapid when compared to the corrosion of the remainder of the steel support.

Steel corrosion is well-known to be an electrochemical process as set forth in U.S. Pat. No. 3,992,272. This reference relates that steel will not corrode at a high pH of 11–13 and suggests that concrete be used to cover stress and corrosion active areas to maintain steel at a pH between 11 and 13 such that corrosion and corrosion fatigue will not occur and that these areas will draw less current from well-known cathodic systems, thus lowering anode or power requirements.

Sacrificial anode is only one means of protection known to the art. Such anodes are inserted on or near the steel member and a portion of the corrosion is thus transferred to the more readily corroded anodes. While sacrificial anodes are satisfactory for some applications, highly stressed areas will still be subject to corrosion fatigue under a cathodic protection sufficient to protect normal steel members. The disadvantage of these cathodic protection systems is that reliable continuous sources of electrical power are required to protect the steel from corrosion and corrosion fatigue. In addition, in cracks or shadowed areas, the electrical current tends to take the easiest path and thus does not protect critical weld areas.

Another means of protection known to the art is employing a jacket of some non-corrosive material around the support. Normally, such jackets are known to encompass the structure in the area of the splash zone. However in the past, these jackets have been entirely unsatisfactory, because of possible damage to the non-corrosive member thus allowing water to penetrate to the steel beneath the jacket. Once water and especially sea water finds its way between the non-corrosive member and the steel member a galvanic cell is formed in which the steel is the sacrificial member to protect the non-corrosive member from the electronegative reaction. Thus corrosion is actually enhanced locally once water has penetrated to the steel beneath the surrounding jacket.

It is thus clearly seen that all presently known means of protection suffer from some disadvantage. Jacketing support members around welds and in splash areas is entirely satisfactory so long as no water gets beneath the jacket. Thus it would be of great disadvantage in the art to provide a method for continually monitoring of such jackets such that an economical and effective method for the protection of joint areas and splash zone areas supporting offshore platforms could be found.

It is therefore an object of the instant invention to provide such a system for monitoring corrosion prevention sheaths. Other objects will become apparent to those skilled in this art as the description proceeds.

It has now been discovered that the corrosion prevention sheaths around submerged weld areas and splash zone areas of offshore platforms can be easily monitored by (a) applying a substantially rigid, fluid impermeable sheath over the area to be protected; (b) sealing the sheath to the area to be protected so as to exclude surrounding fluid medium; (c) providing a fluid passageway in fluid communication from the cavity formed between the sheath and the member to be protected to a vacuum source and to a pressure sensor; (d) reducing pressure in the sealed system below ambient (vacuum); and (e) monitoring the pressure in the system with the pressure sensor, such that a defect thereafter forming in the sheath allows entrance of fluid from the environment and is detected by the pressure sensor, indicating a loss of protection afforded by the sheath.

Thus it can be seen that continuous monitoring of protectant sheaths is provided for offshore platforms where structural steel members and piping systems located in the splash zone and containing weld areas are subject to severe corrosion. When non-corrosive sheaths are used as corrosion protection, the sheaths are sealed to the steel by welding around the edge of the alloy to seal the alloy to the steel. Such welds are preferably exposed to corrosion as compared to structural welds, since the sheath welds are made at much lower temperatures, do not penetrate the support as deeply, and are thus subject to much lower corrosion than the structural weld itself. The instant invention provides a test method and monitoring system to insure that the welds in protective sheaths contain no leaks and to alert a remote detector in case of damage by service vessels and the like. This invention also provides a simple, reliable method for detecting, preventing and retarding corrosion and corrosion fatigue of welded joints or other local critical areas subject to a corrosive environment.

Using the instant invention, any leak into the sheath system will be detected by a change in pressure and can be remotely detected. The system may be easily applied to existing structures, although the preferred method would be to apply the system during the fabrication of new structures under more controllable conditions.

In the past, inspection and testing for leaks in protected sheaths generally consists of a visual inspection carried out by applying a small positive air pressure and visually inspecting for leaks at the time of fabrication. Consequently, it is very unlikely that small cracks would be found. Generally, failures resulting from in service damage are not subjected to inspection. In addition, the use of a positive air pressure unduly complicates monitoring, since leaks in a sheath 800 to 1000 feet below the surface will require a different pressure for detection than those just immediately below the surface and detecting changes in a system of varying pressures is difficult. Use of a sufficiently high pressure for detection of leaks at very deep portions of the platform will result in undesirable pressures in sheaths at or near the surface of the water. By the use of a vacuum as described in the instant invention, such positive pressure system disadvantages are overcome.

Areas not protected by the non-corrosive sheaths can be protected using well-known cathodic potential methods.

Representative patents of the prior art are U.S. Pat. Nos. 3,490,268; 3,043,129; 3,813,921; 3,995,472; 3,518,879; 3,041,834; and 3,505,820. However, none of these references teach or suggest the benefits to be obtained from this combination of vacuum monitored test systems.

The invention is more concretely described with reference to the drawings. Briefly described, the figures show various configurations for rigid and semi-rigid sheaths protecting corrosion prone areas of offshore platforms.

Briefly, FIG. 1 illustrates a cross-section of an offshore platform having the apparatus of the instant invention implaced thereupon. A platform (1) rests upon and is affixed to a sea floor (2) with its major portions submerged below the water level at low tide (10). The platform comprises various members including deck members, bracing members (3) leg members (4). These members are joined together to form the platform by welds (16) as in the joint between members (3) and (4). These are connected by vacuum lines (9) to a central manifold and controller (11) and also in fluid communication with the vacuum source and monitor (12).

FIG. 2 illustrates a cross-section of a support member joined by welds (16). Also included is a heat affected zone (5) which surrounds a weld and which is extremely subject to corrosion and corrosion fatigue. Also in the figure is a sheath of non-corrosive material (12) such as a copper-nickel alloy sheath exemplified in the instant invention. The sheath is sealed in a fluid impermeable manner to the member (4) by means of a second weld (20) or by sealing which holds the sheath in position. A sealed fluid passageway (22) penetrates the sealant or weld to provide open fluid communication between the vacuum manifold and controller (11) exemplified in FIG. 1 and the annulus (24) between the sheath (12) and the support member (4). Damage to the sheath member or sealing means allowing communication with the environment will immediately raise the ambient pressure between the sheath and the support member and activate an alarm indicating that the integrity of the system has been violated.

FIG. 3 illustrates another embodiment of the invention, the figure illustrating a support member (4) being surrounded by a sheath (12) which is semi-rigid in nature and which will partially collapse upon the support members once the pressure between the sheath and the member is reduced. The sheath is comprised of a substantially flexible yet fluid impermeable material and surrounds the welds (16) and heat affected areas (5). In addition, in the figure, the entire splash zone (30) is covered by the sheath so as to prevent corrosion in these highly corrosive areas. Seals or welds (20) are in place so as to provide a fluid tight environment under the sheath. Once the ambient pressure is reduced, the sheath will collapse upon the support member to a small extent, in many cases forming a fluid tight bond such that a single detector (22) will be unable to detect failures in remote portions of the system. In such an event it will be necessary to provide a permeable material to the area as described. The permeable material is represented by (28) and can comprise any fluid permeable material with sufficient structural strength to withstand the collapse of the semi-rigid sheath onto the support member. Representative examples of such materials are braided rope and wire rope. Certain papers can also be used.

When using a semi-rigid material subject to collapse upon lowering of the pressure between the sheath and the support member, an alternative to the use of the fluid impermeable material is a corrugated or rigid underside or an underside having small protrusions such that the material does not collapse entirely upon the support member, thus allowing fluid communication with remote parts of the sheath.

Thus the instant invention also provides a method for protecting a critical area of a structural member subject to corrosion and corrosion fatigue when using a semi-rigid sheath comprising (a) applying a fluid permeable material to the area to be protected as desired; (b) providing a fluid passageway in fluid communication from the permeable material to a vacuum source in pressure sensor, (c) placing an impermeable, semi-rigid covering over the critical area, a permeable sheath, overlying the end of the fluid passageway, and sealing the foregoing from the external environment; (d) reducing pressure in the sealed system below ambient (vacuum); and (e) monitoring the pressure in the system with the pressure sensor such that a defect thereafter forming in the coating allows the entrance of fluid from the environment and is detected by the pressure sensor indicating a loss of the protection afforded by the coating.

Normally the sheathing covers the stressed area and high corrosion area, and when the semi-rigid sheath is used, the fluid permeable material will normally monitor at least 50% of the area leaving no more preferably than 20% of the stressed area out of vacuum communication with the detector system. It should also be emphasized that the fluid permeable materials may be omitted from beneath the semi-rigid sheaths should sheaths be provided with protrusion such that fluid communication with all parts of the sheathed protected area are available to the fluid communication tube.

While the invention is described in relationship to offshore platforms, and is particularly described as securing protective sheaths to structural members by weld joints, it should be realized that the instant invention is applicable to many other uses. For example, the protected areas can include heat affected zones and weld joints of structural members, both above and below the surface of the water. In normal use, the monitored area will be below the surface of the water and the sensor will be above.

In all uses, however, the sensor will normally be designed to activate an alarm upon loss of vacuum in the system. The alarm system can be connected to a plurality of critical areas which are monitored with a common vacuum passageway and wherein the alarm is activated by the sensor upon the predetermined loss of vacuum.

Representative examples of materials suitable for sheathing critical members of offshore platforms are nickel-copper alloys, copper-nickel alloys, and various non-corrosive metallic foils overlying a fluid permeable material. Examples of non-metallic sheathings are fiberglass reinforced polyester resins, epoxy faced coatings and rubber compounds.

When metallic sheaths having a gauge acceptable for welding are placed over the critical areas, normally welding will be an acceptable method for sealing the sheath to the member since such low-temperature welds are much less subject to corrosion than structural welds. However, when metal foils or fiberglass are used it is necessary to seal the sheathing protecting the critical area from the ambient environment using means such as sealants and/or rubber seals. Representative examples of such methods are "o" rings, inflatable seals, epoxy sealants, and heat, radiation, and air cureable elastromers.

It is thus apparent that the instant invention provides a method for continuous monitoring of a high corrosion area and provides immediate detection of protection system failures.

In one embodiment, the monitoring system could be designed to force positive pressure (above ambient) through the fluid line once a leak is detected. This positive pressure would prevent fluid from entering the annulus and forming a galvanic cell to enhance corrosion. Such positive pressure could be used to exclude the external environment until repairs could be made. Preferably, the positive pressure fluid would be an inert gas such as carbon dioxide or nitrogen, although air is preferable to no exclusion whatsoever.

While certain embodiments and details have been shown for the purpose of illustrating this invention, it will be apparent to those skilled in this art that various changes and modifications may be made herein without departing from the spirit or the scope of the invention.

We claim:

1. A method for protecting a critical area of a structural member subject to stress corrosion, and corrosion fatigue comprising,
   (a) placing a fluid impermeable covering over the critical area;
   (b) providing a fluid passageway and fluid communication from the permeable covering to a vacuum source and to a pressure sensor; (c) sealing the foregoing from the external environment and reducing the pressure in the now sealed system below ambient (pressure); and (d) monitoring the pressure in the system with the pressure sensor such that subsequent penetration of the covering allows entrance of fluid from the environment and is detected by the pressure sensor, indicating a loss of protection afforded by the covering.

2. A method of claim 1 wherein the structural member is part of an offshore platform and is secured to other structural joint members by welded joints, and wherein the protected area includes the heat effected zone and weld joint joining the structural member to another member of the offshore platform.

3. A method of claim 2 wherein the protected area is below the surface of the water and wherein the sensor is above the surface of the water.

4. A method of claim 3 further comprising activating an alarm when ambient pressure enters the system.

5. A method of claim 4 wherein a plurality of critical areas are monitored with a common vacuum passageway and wherein an alarm is activated by the sensor upon a predetermined loss of vacuum.

6. The method of claim 5 wherein the critical area monitored is below the surface of the water wherein the vacuum sensor is above the surface of the water and wherein an insulated electrical conductor is passed through the vacuum passageway for at least the distance to above the surface of the water.

7. The method of claim 6 wherein an inert gas under sufficient positive pressure to exclude the external environment is forced into the annulus between the protective sheath and the structural member once loss of vacuum in the system occurs.

8. A method for protecting a critical area of a structural member subject to stress from corrosion comprising (a) applying a permeable material to the critical area as desired; (b) providing a fluid passageway in fluid communication from the permeable material to a vacuum source and to a pressure sensor; (c) placing an impermeable semi-rigid covering over the critical area, the permeable material and the end of the fluid passageway underlying the impermeable covering, and sealing the foregoing from the external environment; (d) reducing pressure in the sealed system below ambient (pressure); and (e) monitoring the pressure in the system with the pressure sensor such that a defect thereafter forming in the covering allows entrance of fluid from the environment and is detected by the pressure sensor indicating a loss of the protection afforded by the covering.

9. A method of claim 8 wherein the covering essentially covers the stressed area and wherein the permeable material forms a pattern monitoring at least 50% of the stressed area such that no area comprising more than about 20% of the stressed area is not in vacuum communication with the sealed system via the fluid permeable material.

* * * * *